(12) United States Patent
Hwang et al.

(10) Patent No.: US 10,136,912 B2
(45) Date of Patent: Nov. 27, 2018

(54) METHOD, APPARATUS, AND SYSTEM FOR GENERATING ULTRASOUND

(71) Applicant: Samsung Electronics Co., Ltd., Suwon-si (KR)

(72) Inventors: Young-kyoo Hwang, Seoul (KR); Won-chul Bang, Seongnam-si (KR); Ho-taik Lee, Yongin-si (KR); Sang-hyun Kim, Hwaseong-si (KR); Ji-young Park, Yongin-si (KR); Do-kyoon Kim, Seongnam-si (KR); Chang-yeong Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 948 days.

(21) Appl. No.: 14/196,901

(22) Filed: Mar. 4, 2014

(65) Prior Publication Data

US 2014/0371774 A1 Dec. 18, 2014

(30) Foreign Application Priority Data

Jun. 18, 2013 (KR) ........................ 10-2013-0069958

(51) Int. Cl.
*A61B 8/00* (2006.01)
*A61B 17/32* (2006.01)
(Continued)

(52) U.S. Cl.
CPC .... *A61B 17/320068* (2013.01); *A61B 8/0858* (2013.01); *A61N 7/02* (2013.01);
(Continued)

(58) Field of Classification Search
CPC .................................................. A61B 8/0858
See application file for complete search history.

(56) References Cited

U.S. PATENT DOCUMENTS

2004/0039285 A1* 2/2004 Ustuner ............... A61B 8/0825
600/459
2004/0122323 A1* 6/2004 Vortman .................. A61N 7/02
600/459

(Continued)

FOREIGN PATENT DOCUMENTS

EP           1 847 294 A1    10/2007
JP         2012-080948 A      4/2012

(Continued)

OTHER PUBLICATIONS

Extended European Search Report dated Oct. 22, 2014 in counterpart European Application No. 13 19 3911 (7 pages, in English).

(Continued)

*Primary Examiner* — Rajeev Siripurapu
(74) *Attorney, Agent, or Firm* — NSIP Law

(57) ABSTRACT

An apparatus and a method are provided to generate an ultrasound to be transmitted from an ultrasound irradiation device. The apparatus and the method include acquiring a medical image including anatomical information about a subject, and calculating characteristics of a tissue in the subject, which may affect propagation of the ultrasound based on the medical image. The apparatus and method also determine a parameter of the ultrasound to create a focal point on the subject using the calculated characteristics, and generate the ultrasound according to the determined parameter.

23 Claims, 8 Drawing Sheets

(51) Int. Cl.
*A61B 8/08* (2006.01)
*A61N 7/02* (2006.01)
*A61B 17/00* (2006.01)
*A61B 34/10* (2016.01)
*A61B 90/00* (2016.01)

(52) U.S. Cl.
CPC .............. *A61B 2017/00106* (2013.01); *A61B 2034/101* (2016.02); *A61B 2090/364* (2016.02); *A61B 2090/374* (2016.02); *A61B 2090/378* (2016.02)

(56) References Cited

U.S. PATENT DOCUMENTS

| 2008/0114274 | A1 | 5/2008 | Moonen et al. |
| 2009/0048514 | A1 | 2/2009 | Azhari et al. |
| 2010/0210940 | A1 | 8/2010 | Bradley et al. |
| 2010/0210976 | A1 | 8/2010 | Darlington et al. |
| 2013/0079681 | A1 | 3/2013 | Park et al. |

FOREIGN PATENT DOCUMENTS

| JP | 5255964 | B2 | 8/2013 | |
| KR | 10-2007-0107089 | A | 11/2007 | |
| KR | 10-2012-0032492 | A | 4/2012 | |
| WO | WO 2013005136 | A1 * | 1/2013 | ......... G01S 7/52049 |

OTHER PUBLICATIONS

Christelle Guittet, et al. "High-frequency estimation of the ultrasonic attenuation coefficient slope obtained in human skin: simulation and in vivo results." *Ultrasound in medicine & biology* 25.3 (1999): 421-429.

Wolfgang Wein, et al. "Automatic CT-ultrasound registration for diagnostic imaging and image-guided intervention." *Medical image analysis* 12.5 (2008): 577-585.

Waag, R. et al., "Cross-sectional measurements and extrapolations of ultrasonic fields," IEEE transactions on sonics and ultrasonics, vol. 32.1, Jan. 1985 (pp. 26-35).

Emad S. Ebbini, et al., "Multiple-Focus Ultrasound Phased-Array Pattern Synthesis: Optimal Driving-Signal Distributions for Hyperthermia," *IEEE Transactions on Ultrasonics Ferroelectrics, and Frequency Control*, vol. 36, No. 5, Sep. 1989, pp. 540-548.

Roel Deckers, et al., "Image-guided, noninvasive, spatiotemporal control of gene expression," *PNAS—Proceedings of the National Academy of Sciences of the United States of America*, Jan. 2009, vol. 106, No. 4, pp. 1175-1180.

* cited by examiner

FIG. 7

| material | CT number (HU) | density (kg/m³) | speed of sound (m/s) | Attenuation (dB/(MHz·cm)) | Acoustic Impedance (kg/m²/sec)× $10^6$ |
|---|---|---|---|---|---|
| Fat | -100~-50 | 950 | 1440-1490 | 0.48 | 1.38 |
| Bone | 1000 | 1912 | 4080 | 6.9~9.94 | 7.8 |

METHOD, APPARATUS, AND SYSTEM FOR GENERATING ULTRASOUND

CROSS-REFERENCE TO RELATED APPLICATIONS

This application claims the benefit of Korean Patent Application No. 10-2013-0069958, filed on Jun. 18, 2013, in the Korean Intellectual Property Office, the disclosure of which is incorporated herein in its entirety by reference.

BACKGROUND

1. Field

The present disclosure relates to methods, apparatus, and a high-intensity focused ultrasound (HIFU) system for generating ultrasound.

2. Description of Related Art

With the advancement of medical science, techniques for local treatment of tumors have been developed from invasive surgery, such as open surgery, to minimal-invasive surgery. A recently developed method is a non-invasive surgery using a gamma knife, a cyber knife, and a high-intensity focused ultrasound (HIFU) knife. The HIFU knife using ultrasound has been widely used in commercial applications as part of a treatment that is environment-friendly and harmless to the human body.

A treatment using a HIFU knife includes focusing and irradiating HIFU on a desired region of a tumor to cause focal destruction or necrosis of tumor tissue and removing and treating the tumor.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Provided are methods, apparatuses, and systems to generate ultrasound. Provided also are non-transitory computer-readable recording media having recorded thereon programs for executing the method on a computer. Technical challenges to be solved are not limited thereto, and other technical challenges may exist.

In accordance with an illustrative configuration, there is provided a method to generate an ultrasound from an ultrasound irradiation device, the method including acquiring a medical image including anatomical information about a subject; calculating characteristics of a tissue in the subject affecting propagation of the ultrasound based on the medical image; determining a parameter of the ultrasound to create a focal point on the subject using the calculated characteristics; and generating the ultrasound according to the determined parameter.

The calculating of the characteristics may include processing the medical image to calculate the characteristics of the tissue on a path along which the ultrasound propagates from an element of the ultrasound irradiation device to the focal point.

The characteristics may also include a speed of the ultrasound passing through the tissue, a density of the tissue, an attenuation coefficient of the ultrasound for the tissue, or a combination thereof.

The method may also include calibrating the ultrasound irradiation device using the medical image.

The calculating of the characteristics may further include processing the ultrasound irradiation device and the medical image to calculate the characteristics of the tissue along a path that the ultrasound propagates from an element of the ultrasound irradiation device to the focal point.

The calibrating of the ultrasound irradiation device may include generating an ultrasound image of the subject using a diagnostic ultrasound irradiation device; calibrating the diagnostic ultrasound irradiation device using an image obtained by registering the ultrasound image with the medical image; and calibrating the ultrasound irradiation device using the calibrated diagnostic ultrasound irradiation device.

The calibration may be performed by adjusting coordinates of the ultrasound irradiation device.

The medical image may include a computed tomography (CT) image.

The determining of the parameter of the ultrasound may include determining the parameter by combining characteristics of the ultrasound with the calculated characteristics affecting the propagation of the ultrasound.

In accordance with an illustrative configuration, there is provided an apparatus to generate an ultrasound, the apparatus including an interface unit configured to acquire a medical image including anatomical information about a subject; a characteristics calculation unit configured to calculate characteristics of a tissue in the subject affecting propagation of the ultrasound based on the medical image; a parameter determiner configured to determine a parameter of the ultrasound to create a focal point on the subject using the calculated characteristics; and a control unit configured to produce a control signal to generate the ultrasound according to the determined parameter.

The characteristics calculation unit may process the medical image to calculate the characteristics of the tissue on a path along which the ultrasound propagates from an element of a therapeutic ultrasound irradiation device to the focal point.

The characteristics may include a speed of the ultrasound passing through the tissue, a density of the tissue, an attenuation coefficient of the ultrasound for the tissue, or a combination thereof.

The apparatus may also include a calibration unit configured to calibrate the apparatus using the medical image.

The calibration unit may acquire an ultrasound image of the subject from the interface unit, calibrates a diagnostic ultrasound irradiation device by using an image obtained by registering the ultrasound image with the medical image, and calibrates the apparatus by using the calibrated diagnostic ultrasound irradiation device.

The medical image may include a computed tomography (CT) image.

A non-transitory computer-readable recording medium having recorded thereon a program for executing the method as described above.

In accordance with an illustrative configuration, there is provided a method to generate an ultrasound, the method including acquiring an image of a subject including heterogeneous tissue; and determining a parameter of the ultrasound, in which characteristics of the heterogeneous tissue has been reflected using the image.

The image of the subject may include human internal organs.

The determining of the parameter of the ultrasound includes calculating characteristics of the heterogeneous tissue affecting propagation of the ultrasound using the image; and determining the parameter of the ultrasound to create a focal point on the subject using the calculated characteristics.

The determining of the parameter of the ultrasound using the calculated characteristics includes calculating a first sound pressure representing a sound pressure at the focal point when the ultrasound propagates in homogeneous tissue; determining an element that transmits the ultrasound among elements in the ultrasound irradiation device and setting a particle velocity of the determined element; calculating a second sound pressure representing a sound pressure at the focal point when the ultrasound using the particle velocity propagates in the heterogeneous tissue; and determining the parameter of the ultrasound based on a relationship between the first sound pressure and the second sound pressure.

The determining of the parameter of the ultrasound based on the relationship between the first and second sound pressures may include determining whether a difference between the first and second sound pressures exceeds a threshold value; and resetting a particle velocity of the element in response to the difference exceeding the threshold value.

In accordance with an illustrative configuration, there is provided an ultrasound control apparatus, including a processor configured to process a medical image of a subject to determine a parameter based on a speed of a therapeutic ultrasound passing through a tissue, a density of the tissue, and an attenuation coefficient and to control the therapeutic ultrasound to create a focal point onto a subject; and a controller producing a signal to generate ultrasound waves according to the determined parameter.

The characteristics calculation unit may be further configured to control an intensity and a duration of the therapeutic ultrasound. The apparatus may also include a calibration unit processing the medical image to calibrate the processor and the controller.

Other features and aspects may be apparent from the following detailed description, the drawings, and the claims.

BRIEF DESCRIPTION OF THE DRAWINGS

These and/or other aspects will become apparent and more readily appreciated from the following description of the embodiments, taken in conjunction with the accompanying drawings in which:

FIG. 7 is an example of a table model generated by a second model generator, according to an embodiment;

Figure 1:
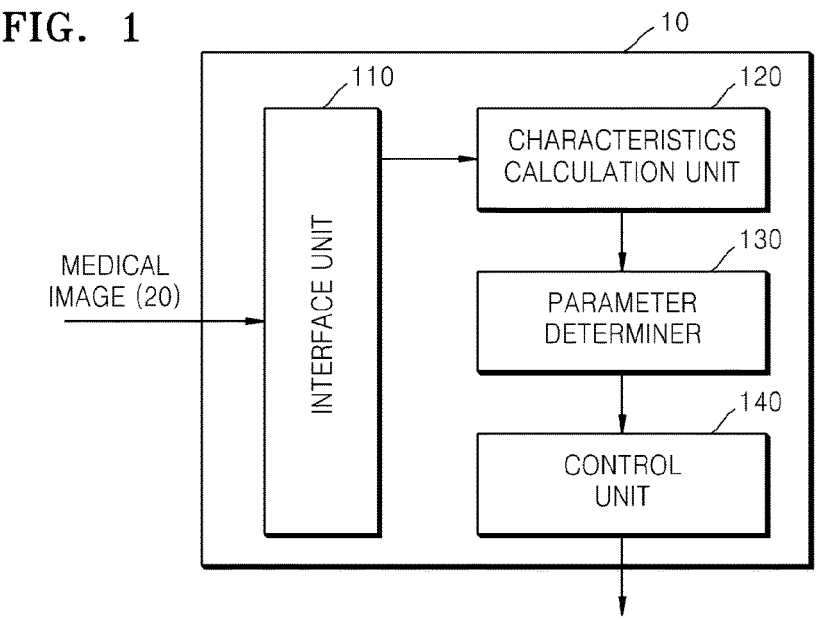
FIG. 1 illustrates a configuration of an apparatus to control ultrasound, according to an embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness. Expressions such as "at least one of," when preceding a list of elements, modify the entire list of elements and do not modify the individual elements of the list.

FIG. 1 illustrates an apparatus 10 to control ultrasound (hereinafter, referred to as "ultrasound control apparatus"), according to an embodiment. Referring to FIG. 1, the ultrasound control apparatus 10, according to an illustrative example, includes an interface unit 110, a characteristics calculation unit 120, a parameter determiner 130, and a control unit 140.

Although the ultrasound control apparatus 10 of FIG. 1 includes certain components, it will be understood by those skilled in the art that the ultrasound control apparatus 10 may further include additional components to the components shown in FIG. 1. Also, in an alternative configuration, the ultrasound control apparatus 10 may exclude, for instance, the interface unit 110 and the characteristic calculation unit 120 may include an interface to receive a signal representative of a medical image. The ultrasound control apparatus 10 may correspond to one or more processors.

As illustrated in FIG. 1, the interface unit 110 acquires a medical image 20 including anatomical information about a subject. The object may include at least one tissue of a patient. For example, the object may be a heterogeneous part of a human body, which includes different kinds of tissues such as skin, bone, muscle, blood, and an organ, or a combination thereof, but is not limited thereto. The anatomical information about the object may be information about locations and sizes of one or more tissues. A therapeutic ultrasound irradiation device (not shown) may create a focal point of therapeutic ultrasound at a target position of the object to generate the medical image 20.

The medical image 20 may be a previously acquired and stored as a computed tomography (CT) image or magnetic resonance (MR) image of the object, but is not limited thereto. For example, images that have been previously acquired and stored for the same object, and images acquired just prior to ultrasound treatment may be input to the ultrasound control apparatus 10 through the interface unit 110.

The interface unit 110 may be a unit to perform data input or output or to transmit information directly input by a user to another unit. The characteristics calculation unit 120 processes the medical image 20 to calculate characteristics of one or more tissues in the object that may affect the propagation of therapeutic ultrasound. For example, the characteristics calculation unit 120 receives the medical image 20 from the interface unit 110 to calculate characteristics of one or more tissues in the object that may affect the propagation of therapeutic ultrasound.

Characteristics that may affect the propagation of therapeutic ultrasound may be physical characteristics of each of the one or more tissues. The physical characteristics may include speed of the therapeutic ultrasound passing through each of the tissues, a density of each tissue, an attenuation coefficient of the therapeutic ultrasound for the tissue, or a combination thereof, but are not limited thereto.

Because ultrasound is a radiated wave produced by vibrations through a physical medium, propagation speed of an ultrasound wave is affected by a density of the physical medium. More specifically, as the density of the physical medium increases, a speed of the ultrasound wave increases. Furthermore, as the ultrasound wave travels through the medium, the ultrasound wave may be absorbed or scattered by the medium, thereby reducing its intensity or amplitude. A reduction in intensity or amplitude of the ultrasound wave is called an attenuation of the ultrasound wave. An amount of attenuation of an ultrasound wave is proportional to a frequency of the ultrasound wave and an amount of protein in a tissue through which the ultrasound wave passes. The amount of attenuation of the ultrasound wave is inversely proportional to water content of the tissue. The parameter determiner 130 determines a parameter of therapeutic ultrasound to create a focal point onto a subject using calculated characteristics. For example, the parameter determiner 130 receives the calculated characteristics from the characteristics calculation unit 120 and determines a parameter to irradiate the therapeutic ultrasound on the focal point by using the characteristics.

The control unit 140 produces a signal to generate ultrasound waves according to the determined parameter. For example, the control unit 140 receives the parameter determined by the parameter determiner 130 to generate a control signal for a therapeutic ultrasound irradiation device 30 as shown in FIG. 2.

The ultrasound control apparatus 10 having the above-described configuration calculates the speed of therapeutic ultrasound passing through tissue, a density of the tissue, and an attenuation coefficient of therapeutic ultrasound and precisely control the therapeutic ultrasound so that a therapeutic ultrasound irradiation device creates a focal point at a desired position. The ultrasound control apparatus 10 may also control the intensity and duration of therapeutic ultrasound being transmitted.

Figure 2:
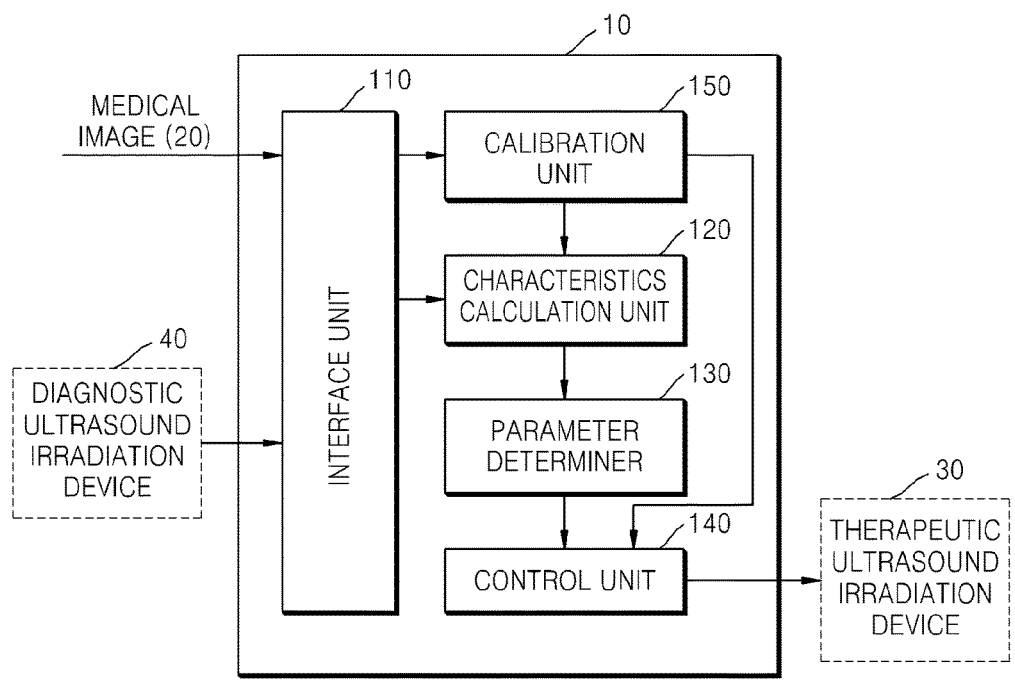
FIG. 2 illustrates a configuration of an apparatus to control ultrasound according to another embodiment.

FIG. 2 illustrates a configuration of an ultrasound control apparatus 10 according to another embodiment. Referring to FIG. 2, the ultrasound control apparatus 10 includes an interface unit 110, a characteristics calculation unit 120, a parameter determiner 130, a control unit 140, and a calibration unit 150.

Although the ultrasound control apparatus 10 of FIG. 2 includes certain components, it will be understood by those skilled in the art that the ultrasound control apparatus 10 may further include additional components to the components shown in FIG. 2. Also, in an alternative configuration, the ultrasound control apparatus 10 may exclude, for instance, the interface unit 110 and the calibration unit 150 and the characteristic calculation unit 120 may include an interface to receive a signal representative of a medical image. The ultrasound control apparatus 10 of FIG. 2 may correspond to one or more processors.

The interface unit 110 acquires an ultrasound image of a subject from a diagnostic ultrasound irradiation device 40. The interface unit 110, the characteristics calculation unit 120, the parameter determiner 130, and the control unit 140 have substantially the same functions as those of their counterparts in FIG. 1.

The diagnostic ultrasound irradiation device 40 transmits diagnostic ultrasound to a subject and acquires an ultrasound signal reflected from the subject. More specifically, in response to the diagnostic ultrasound irradiation device 40 transmitting a diagnostic ultrasound having a frequency range of 2 to 18 MHz to the subject, the diagnostic ultrasound is partially reflected from layers between different tissues of the subject. The diagnostic ultrasound is reflected from an area of the subject where there is a change in density, for instance, from blood cells within a blood plasma or small structures within organs. The reflected diagnostic ultrasound vibrates a piezoelectric converter of the diagnostic ultrasound irradiation device 40. As the piezoelectric converter vibrates, it emits electrical pulses producing the ultrasound signal.

The diagnostic ultrasound irradiation device 40 converts or processes the ultrasound signal to an ultrasound image of the subject to be then transmitted to the interface unit 110. For instance, the diagnostic ultrasound irradiation device 40 directly generates ultrasound images of the subject using electrical pulse signals, or the calibration unit 150, which will be described below, produces ultrasound images of the subject by using the electrical pulse signals. When the diagnostic ultrasound irradiation device 40 directly generates ultrasound images, the diagnostic ultrasound irradiation device 40 transmits information about the ultrasound images to the interface unit 110. On the other hand, when the calibration unit 150 generates ultrasound images, the diagnostic ultrasound irradiation device 40 transmits the electrical pulse signals to the interface unit 110.

In addition, the diagnostic ultrasound irradiation device 40 has a particular location relationship with a therapeutic ultrasound irradiation device 30. For example, the diagnostic ultrasound irradiation device 40 and the therapeutic ultrasound irradiation device 30 may be separated from each other with a predetermined distance interposed therebetween for operation, may be located adjacent to each other, or may be integrated as a single device.

Although not shown in FIG. 2, the therapeutic ultrasound irradiation device 30 may include a combination of one or more elements. When the therapeutic ultrasound irradiation device 30 includes a plurality of elements, the plurality of elements receive signals from the control unit 140 to individually transmit therapeutic ultrasound waves. Furthermore, durations of transmission of the therapeutic ultrasound may be set differently for each of the elements. Because the plurality of elements may individually transmit therapeutic ultrasound as described above, it is possible to change a position of a focal point of the therapeutic ultrasound while the therapeutic ultrasound irradiation device 30 remains stationary. Thus, therapeutic ultrasound may be focused along lesions of an internal organ moving due to a patient's respiration or other motions. For example, the therapeutic ultrasound irradiation device 30 may converge therapeutic ultrasound on a focal point by using a phase array technique. The phase array technique is understood by those skilled in the art, and a detailed description thereof is omitted. In one example, therapeutic ultrasound may be high intensity focused ultrasound (HIFU) having enough energy to cause necrosis of a tumor inside a patient's body. A HIFU system focuses and irradiates HIFU onto a portion of a subject to be treated to cause focal destruction or necrosis of a lesion and removes or treats the lesion.

When the therapeutic ultrasound irradiation device 30 in the HIFU system continues to irradiate the focal point by adjusting the focal point of the HIFU to a certain position, the temperature of a cell irradiated with HIFU rises above a predetermined temperature to cause necrosis of the surrounding tissue. The description of the present embodiment may also apply to other devices that transmit focused ultrasound similar to HIFU or devices to adjust a focal point using a sound pressure.

The calibration unit 150 uses the medical image 20 to calibrate the diagnostic ultrasound irradiation device 30, through the control unit 140, to transmit therapeutic ultrasound. The calibration refers to a process of adjusting coordinates of the therapeutic ultrasound irradiation device 30 so that the therapeutic ultrasound irradiation device 30 may transmit the therapeutic ultrasound to a point corresponding to a predetermined point (for instance, a lesion) within the medical image 20.

Figure 3:
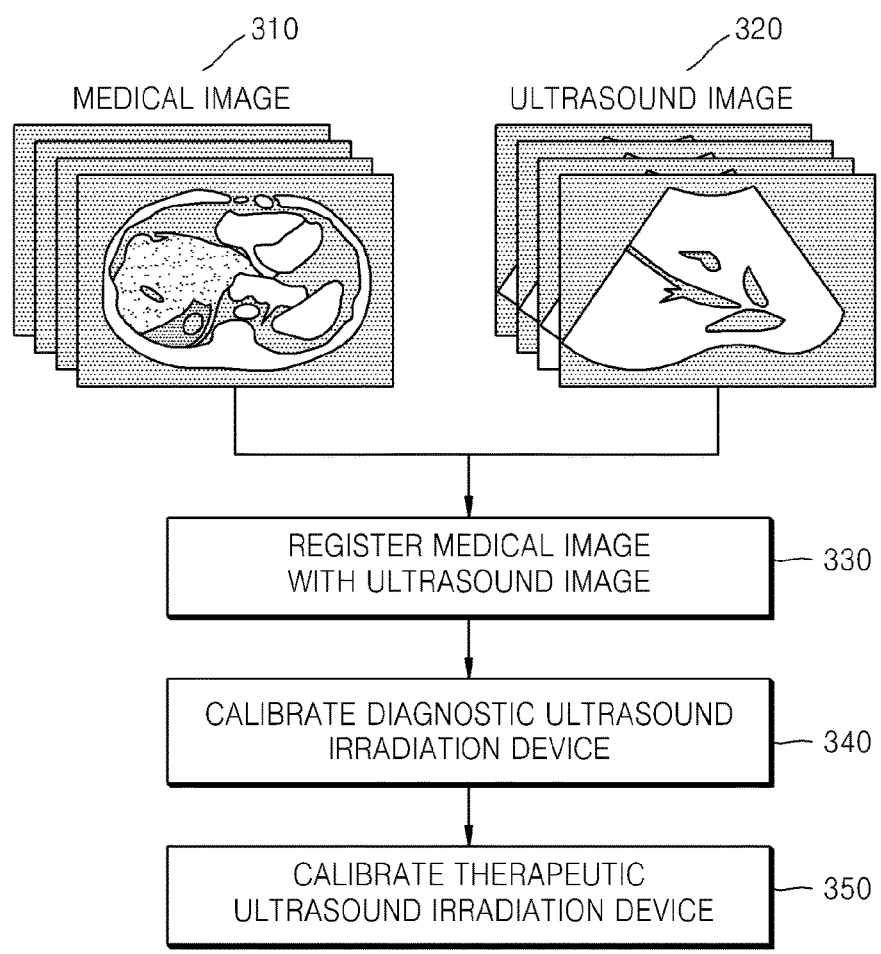
FIG. 3 illustrates a method of calibrating a therapeutic ultrasound irradiation device in a calibration unit, according to an embodiment.

FIG. 3 illustrates a method of calibrating the therapeutic ultrasound irradiation device 30 in the calibration unit 150. It is assumed herein that medical images 310 are computed tomography (CT) images, but other types of medical images may be provided.

The calibration unit 150 receives electrical pulse signals from the interface unit 110 to generate ultrasound images 320 of a subject. In this case, the calibration unit 150 may use the electrical pulse signals to generate two-dimensional (2D) or three-dimensional (3D) ultrasound images of the subject. For example, the diagnostic ultrasound irradiation device 40 irradiates the subject with diagnostic ultrasound by changing a location and an orientation of the subject, receives a reflected ultrasound, and transmits electrical pulse signals corresponding to the reflected ultrasound to the interface unit 110. The calibration unit 150 uses the electrical pulse signals received from the interface unit 110 to generate a plurality of cross-sectional images of the subject. The calibration unit 150 then accumulates the plurality of cross-sectional images to create a 3D ultrasound image of the subject.

In response to the diagnostic ultrasound irradiation device 40 generating ultrasound images, the calibration unit 150 acquires the ultrasound images through the interface unit 110.

As illustrated in FIG. 3, at operation 330, the method at the calibration unit 150 registers the medical image 310 received from the interface unit 110 with the ultrasound image 320 of the subject. The registration refers to a method of configuring a first coordinate system of the medical image 310 to correspond to a second coordinate system of the ultrasound image 320. An image obtained after the registration may be a single medical image into which the medical image 310 and the ultrasound image 320 are combined, or an image in which the medical image 310 and the ultrasound image 320, having the same coordinate system, are disposed in parallel.

In one example, the calibration unit 150 registers the medical images 310 with the ultrasound images 320 using geometrical correlations between tissues in the medical images 310 and those in the ultrasound images 320. The geometrical correlations may be relationships between landmark points extracted from the tissues. The calibration unit 150 may determine a point at which anatomical structure of tissue is distinctly reflected as a landmark point. For example, if a tissue of interest from which a landmark point will be extracted is a liver, a point at which blood vessels branch off in a vascular structure of the liver may be determined as the landmark point. If the tissue of interest is a heart, the landmark point may be a boundary between the right and left atria or a boundary where the vena cava and an outer wall of the heart meet.

In another example, the calibration unit 150 may determine an uppermost or a lowermost point of tissue in a predetermined coordinate system as a landmark point.

In another example, the calibration unit 150 may also determine uniformly spaced points, which can be interpolated between the landmark points selected in the above examples, as landmark points.

Referring to FIG. 3, at operation 330, the method at the calibration unit 150 registers the ultrasound image 320 with the medical image 310 and calculates a transformation relation between the first coordinate system of the medical image 310 and the second coordinate system of the ultrasound image 310. For example, the calibration unit 150 finds points in the ultrasound image 320 corresponding to points in the medical image 310, respectively, and calculates a coordinate transformation matrix to map any point in the medical image 310 to the corresponding point in the ultrasound image 320.

In one example, the calibration unit 150 may set coordinates of a predetermined position Pi (xi, yi, zi), for instance, a position at which a focal point of therapeutic ultrasound is to be formed, in the medical image 310 with respect to its arbitrary origin. The method at the calibration unit 150 then registers the ultrasound image 320 with the medical image 310 (operation 330) and finds coordinates of a point Pt(xt, yt, zt) in the ultrasound image 320 corresponding to the coordinates of the position Pi(xi, yi, zi) through the registration. The calibration unit 150 calculates variations $\Delta x$, $\Delta y$, and $\Delta z$ in positions of the points Pi and Pt along x-, y-, and z-axes. According to a process described above, at operation 340, the method at the calibration unit 150 calibrates the diagnostic ultrasound irradiation device 40.

At operation 350, the method at the calibration unit 150 uses the calibrated diagnostic ultrasound irradiation device 40 to calibrate the therapeutic ultrasound irradiation device 30. The calibration is a method of adjusting coordinates of the therapeutic ultrasound irradiation device 30 so that the therapeutic ultrasound irradiation device 30 transmits therapeutic ultrasound to a point corresponding to a predetermined point within the medical image 310.

In one example, the diagnostic ultrasound irradiation device 40 and the therapeutic ultrasound irradiation device 30 have a predetermined position relationship with each other. Thus, the method at the calibration unit 150 calibrates the therapeutic ultrasound irradiation device 30 based on the known relationship between coordinates of the diagnostic ultrasound irradiation device 40 and the therapeutic ultrasound irradiation device 30.

In this example, the relationship between coordinates of the diagnostic ultrasound irradiation device 40 and the therapeutic ultrasound irradiation device 30 are calculated by rotation and translation of a coordinate axis and enlargement or reduction using a scale factor. The relationship between coordinates of focal points of diagnostic ultrasound and therapeutic ultrasound transmitted from the diagnostic ultrasound irradiation device 40 and the therapeutic ultrasound irradiation device 30, respectively, may be calculated by rotation and translation of a coordinate axis and enlargement or reduction using a scale factor.

For example, the calibration unit 150 calibrates the therapeutic ultrasound irradiation device 30 by calculating a position of a focal point of a therapeutic ultrasound transmitted from the therapeutic ultrasound irradiation device 30 within the ultrasound image 320. The calibration unit 150 calculates the position of the focal point based on the known relationship between coordinates of the diagnostic ultrasound irradiation device 40 and the therapeutic ultrasound irradiation device 30.

Further, the calibration unit 150 calculates a position of a focal point of therapeutic ultrasound to be transmitted from the therapeutic ultrasound irradiation device 30 within the medical image 310.

Referring back to FIG. 2, the calibration unit 150 transmits a generated signal to the control unit 140, and the control unit 140 changes a position to be irradiated by the therapeutic ultrasound irradiation device 30 with therapeutic ultrasound so that the position corresponds to the calibrated coordinates.

The calibration unit 150 calibrates the therapeutic ultrasound irradiation device 30 in this way so that therapeutic ultrasound is transmitted from the therapeutic ultrasound irradiation device 30 to precisely form a focal point at a desired position.

Figure 4:
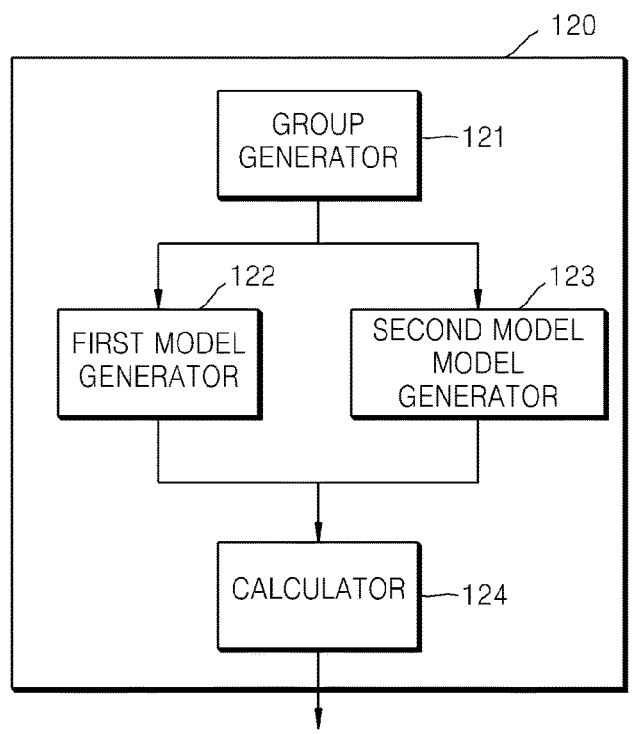
FIG. 4 illustrates an example of a characteristics calculation unit, according to an embodiment.

FIG. 4 illustrates a configuration of the characteristics calculation unit 120, in accord with an embodiment. Referring to FIG. 4, the characteristics calculation unit 120 includes a group generator 121, a first model generator 122, a second model generator 123, and a calculator 124.

Although the characteristics calculation unit 120 of FIG. 4 includes certain components, it will be understood by those skilled in the art that the characteristics calculation unit 120 may further include additional components to the components shown in FIG. 4. The characteristics calculation unit 120 may correspond to one or more processors.

Referring back to FIG. 2, the characteristics calculation unit 120 uses the medical image 20 to calculate characteristics of one or more tissues lying on a path along which therapeutic ultrasound propagates from the therapeutic ultrasound irradiation device 30 to a position of a focal point. For example, the characteristics calculation unit 120 generates models for characteristics of each of the tissues that construct a heterogeneous subject and calculates the characteristics of the one or more tissues on the propagation path using the generated models.

Referring to FIG. 4, the group generator 121 identifies a type of the one or more tissues on a path along which therapeutic ultrasound propagates through the therapeutic ultrasound irradiation device 30 to a position of a focal point.

Figure 5:
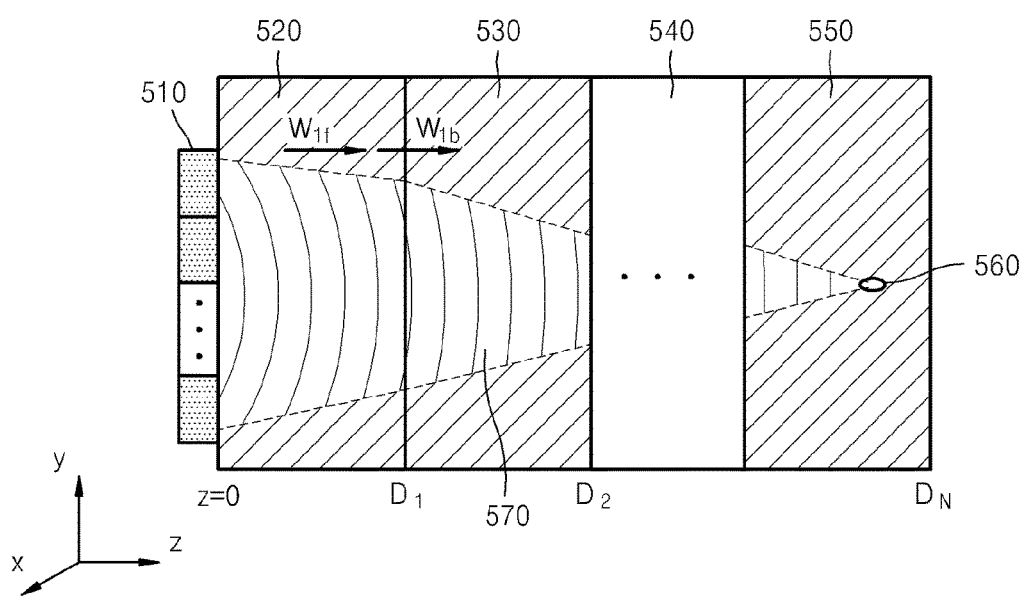
FIG. 5 illustrates an example of a tissue located on a path along which therapeutic ultrasound travels from an element of a therapeutic ultrasound irradiation device to a focal point, according to an embodiment.

FIG. 5 illustrates an example of at least one tissue located on a path along which therapeutic ultrasound propagates through the therapeutic ultrasound irradiation device 30 as shown in FIG. 2) to a position of a focal point.

Referring to FIG. 5, at least one tissue 520 through 550 may be located on a path along which therapeutic ultrasound propagates through an element 510 in the therapeutic ultrasound irradiation device 30 to a focal point 560. For example, the at least one tissue 520 through 550 may include skin, bone, muscle, blood, and an organ.

Referring back to FIG. 4, the group generator 121 identifies the type of the at least one tissue 520 through 550 shown in FIG. 5 on a path along which the therapeutic ultrasound propagates from the element 510 of the calibrated therapeutic ultrasound irradiation device 30 to a position of the focal point 560 using information about the element 510 that is received from the calibration unit 150.

The group generator 121 divides the one or more tissues into a plurality of groups based on the identified types of the tissues. For example, when a medical image is a CT image, the group generator 121 divides the one or more tissues in a subject, lying on the propagation path of the therapeutic ultrasound, into first and second groups based on a CT number obtained from the medical image of each of the tissues.

In one example, the CT number is a value that represents the degree of absorption for each pixel in a CT image. The pixel is a pixel in a 2D image or a voxel in a 3D image. The CT number is a relative X-ray attenuation coefficient determined for each tissue. CT numbers of air, water, and bone are −1000, 0, and +1000, respectively.

The group generator 121 divides the tissues into the first and second groups based on a distribution of the CT numbers. In one example, the group generator 121 determines tissues having the CT numbers in a predetermined range as the first group and tissues having very high or very low CT numbers as the second group.

For example, as known in the art, the CT number of bone is +1000, and the CT number of fat is from about 100 to about −50. The bone has a very high CT number while the fat has a very low CT number compared to the liver (40 to 60 Hu), the kidney (30 Hu), the brain (37 Hu), and blood (40 Hu). Thus, the group generator 121 determines tissues, other than the bone and fat, as the first group and the bone and fat as the second group.

After dividing the tissues into the first and second groups in the manner described above, the group generator 121 transmits information about the tissues in the first group and information about the tissues in the second group to the first model generator 122 and the second model generator 123, respectively.

The first model generator 122 uses CT numbers of the tissues in the first group to generate a first model representing characteristics of each of the tissues in the first group. In one instance, the characteristics are physical characteristics of each of the one or more tissues. The physical characteristics may include the speed of therapeutic ultrasound passing through each of the tissues, a density of each tissue, an attenuation coefficient of therapeutic ultrasound for the tissue, or a combination thereof, but are not limited thereto.

In one embodiment, the first model generator 122 uses CT numbers of the respective tissues in the first group to generate a graph model for the speed of the therapeutic ultrasound passing through the tissues. Alternatively, the first model generator 122 uses the CT numbers of the respective tissues in the first group to generate a table model for the speed of therapeutic ultrasound passing through the tissues.

Figure 6:
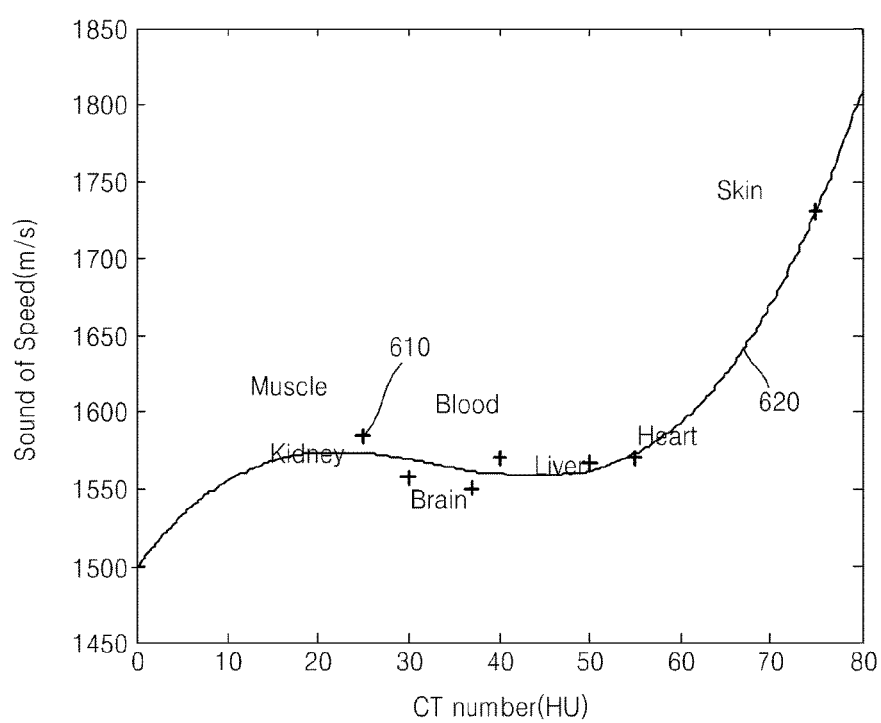
FIG. 6 is an example of a graph model generated by a first model generator, according to an embodiment.

FIG. 6 is an example of a graph model 620 generated by the first model generator 122 shown in FIG. 4, in accord with an embodiment.

The first model generator 122 calculates the speed of therapeutic ultrasound passing through each tissue using Equation (1) below:

$$c = 0.0028h^3 - 0.28h^2 + 8.2313h + 1497.6 \quad (1)$$

where c is the speed of therapeutic ultrasound passing through each tissue (expressed in m/s) and h is a CT number (expressed in Hounsfield units (Hu)) for the tissue.

The first model generator 122 calculates the speed of therapeutic ultrasound for each of the tissues in the first group and approximates the calculated speed to generate the graph model 620 for the speeds of therapeutic ultrasound passing through the tissues.

In another embodiment, the first model generator 122 uses CT numbers corresponding to the respective tissues in the first group to generate a graph model or table model for densities of the tissues. The first model generator may calculate the density of each tissue using the following Equation (2):

$$\rho = 0.00129h^3 - 0.14661h^2 + 5.1286h + 990.34 \quad (2)$$

where $\rho$ is a density of each tissue (expressed in kg/m$^3$), and h is a CT number for the tissue (expressed as Hu).

The first model generator 122 calculates the density of each of the tissues in the first group and approximates the calculated densities to generate a graph model for the densities of the tissues. In this case, the first model generator 122 generates a graph model for the density in the same manner as described above with regards to the generating of the graph model 620 for the speed of therapeutic ultrasound.

In another embodiment, the first model generator 122 uses the CT numbers of the respective tissues in the first group to generate a graph model or table model for attenuation coefficients of therapeutic ultrasound for the tissues. The first model generator 122 calculates an attenuation coefficient of therapeutic ultrasound for each tissue using the following Equation (3):

$$\alpha = 0.0000044h^3 - 0.0045h^2 + 0.13h + 0.022 \quad (3)$$

where $\alpha$ is an attenuation coefficient of therapeutic ultrasound for each tissue (expressed in db/(MHz*cm)), and h is a CT number for the tissue.

The first model generator 122 calculates the attenuation coefficient of the therapeutic ultrasound for each of the tissues in the first group and approximates the calculated attenuation coefficients to generate a graph model for the attenuation coefficients of the therapeutic ultrasound for each of the tissues. In this case, the first model generator 122 may generate a graph model for the attenuation coefficient of the therapeutic ultrasound in the same manner as described above with regards to the generating of the graph model 620 for the speed of therapeutic ultrasound.

The first model generator 122 transmits information about the generated first model to the calculator 124.

Referring to FIG. 4, the second model generator 123 generates a second model representing characteristics of each of the tissues in the second group. In one example, the characteristics are physical characteristics of each of the one or more tissues. The physical characteristics may include the speed of therapeutic ultrasound passing through each of the tissues, a density of each tissue, an attenuation coefficient of therapeutic ultrasound for the tissue, or a combination thereof, but are not limited thereto.

For example, the second model generator 123 generates a table model including the known speed of therapeutic ultrasound passing through each of the tissues (e.g., bone and fat) in the second group, the density of the tissue, and the attenuation coefficient of the therapeutic ultrasound for the tissue.

FIG. 7 is an example of a table model generated by the second model generator 123, in accord with an embodiment.

Referring to FIG. 7, the second model generator 123 generates the table model as a second model that indicates names, CT numbers, densities, and speeds and attenuation coefficients of therapeutic ultrasound for the tissues in the second group.

The second model generator 123 transmits information about the generated second model to the calculator 124.

The characteristics calculation unit 120 outputs a graph model or table model generated in the same manner, as described above, to a display device (not shown) through the interface unit 110.

Although the characteristics calculation unit 120 has been described to include the group generator 121 and the first and second model generators 122 and 123, the embodiment is not limited thereto. For example, Equations (1) through (3) and the table model of FIG. 7 may be stored in the characteristics calculation unit 120 for future use, or operations to generate the first and second models may be performed independently to the operation of the characteristics calculation unit 120.

Referring back to FIG. 4, the calculator 124 uses the graph model and the table model to calculate the characteristics. In one example, the calculator 124 combines information about the graph model received from the first model generator 122 with information about the table model received from the second model generator 123. The calculator 124 also calculates characteristics of one or more tissues on a path along which therapeutic ultrasound propagates from an element of the therapeutic ultrasound irradiation device 30 to a position of a focal point. The calculator 124 transmits information about the calculated characteristics to the parameter determiner 130.

Referring back to FIG. 2, the parameter determiner 130 determines a parameter of the therapeutic ultrasound to create a focal point onto a subject using calculated characteristics. In one example, the parameter determiner 130 determines a parameter by combining predetermined characteristics of the therapeutic ultrasound transmitted from the therapeutic ultrasound irradiation device 30 with the characteristics that the calculator 124 calculated and may affect the propagation of the therapeutic ultrasound.

In this case, the parameter is a combination of variables used to create a focal point of the therapeutic ultrasound. The variables may include, but are not limited to, a frequency, amplitude, phase, peak intensity, pulse length, and duty ratio of the therapeutic ultrasound and the number or positions of elements in the therapeutic ultrasound irradiation device 30.

Figure 10:
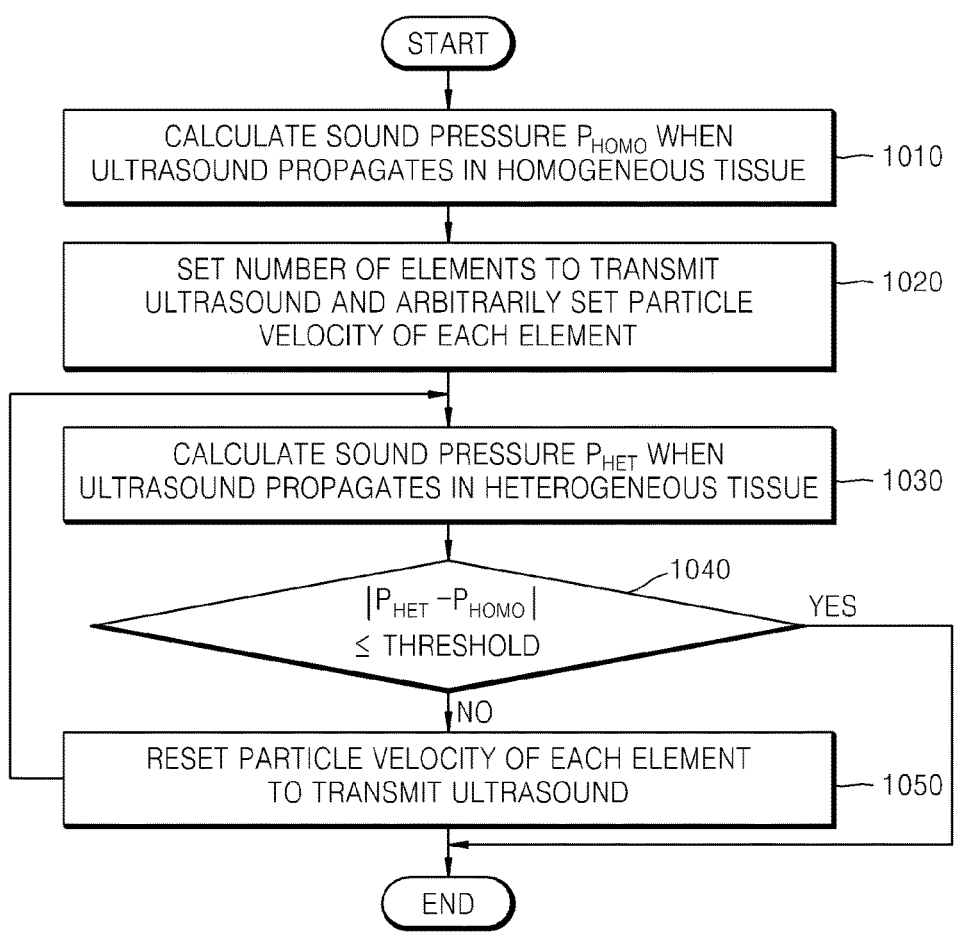
FIG. 10 is a flowchart illustrating an operation of a parameter determiner, according to an embodiment.

FIG. 10 is a flowchart illustrating an example of operation of the parameter determiner 130, in accord with an embodiment.

A medium through which therapeutic ultrasound passes is a heterogeneous medium including several different tissues as shown in FIG. 5. Thus, an embodiment to determine a parameter of therapeutic ultrasound that reflects the effect of a heterogeneous medium so that a focal point is formed at a desired position will now be described with reference to FIG. 10.

Briefly, the method includes calculating a sound pressure $P_{HOMO}$ at a position of a focal point created by the therapeutic ultrasound by assuming that the therapeutic ultrasound travels through a homogeneous medium. The sound pressure $P_{HOMO}$ is also calculated by adjusting a parameter of the therapeutic ultrasound so that the absolute value of a difference between the sound pressure, $P_{HOMO}$, and a sound pressure, $P_{HET}$, at a position of a focal point when the therapeutic ultrasound propagates through a heterogeneous medium is less than or equal to a threshold value. In this example, the parameter of the therapeutic ultrasound may be a particle velocity that represents the amplitude and phase of the therapeutic ultrasound.

Figure 12:
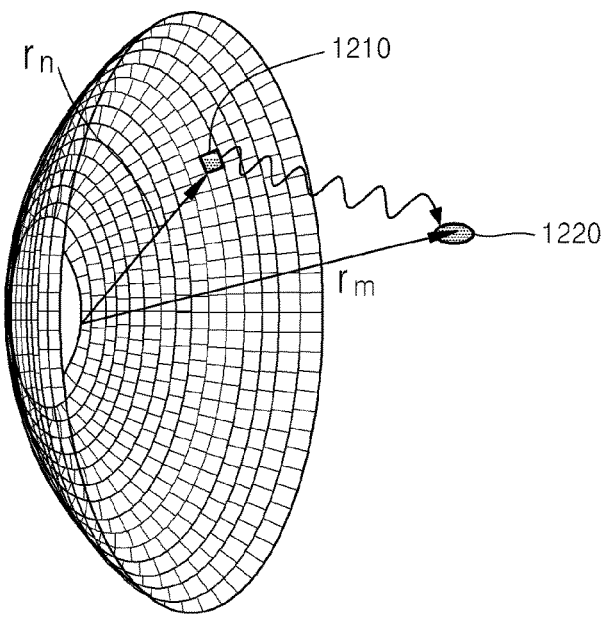
FIG. 12 illustrates a relationship between a focal point and a therapeutic ultrasound irradiation device, according to an embodiment.

FIG. 12 illustrates a relationship between a focal point and the therapeutic ultrasound irradiation device (30 in FIG. 2), according to an embodiment.

In this embodiment, it is assumed that therapeutic ultrasound is transmitted from N elements in the therapeutic ultrasound irradiation device 30 and creates focal points at M target positions. The therapeutic ultrasound irradiation device 30 may include two or more elements, all or some of which transmit the therapeutic ultrasound.

FIG. 12 illustrates position vectors of an n-th element 1210 (n=1, 2, . . . , N) and an m-th focal point position 1220 (m=1, 2, . . . , M). In FIG. 12, $r_n$ is a position vector of the n-th element 1210, and $r_m$ is a position vector of an m-th focal point position 1220.

Referring back to FIG. 10, at operation 1010, when a position of a focal point is specified, the method calculates a sound pressure $P_{HOMO}$ at the position of the focal point by assuming that the therapeutic ultrasound travels through homogeneous tissue. For example, when a position at which a focal point is to be formed is designated, the method at the parameter determiner 130 calculates a particle velocity of each element. In this case, the position of the focal point is specified based on information input from a user through the interface unit 110, or automatically designated by the apparatus 10 as illustrated in FIG. 2 to control an ultrasound automatically, dynamically, or without user intervention.

A phase of the particle velocity may be calculated assuming that the speed of a sound wave is constant generally at 1540 m/s. For example, after computing a time taken for a sound wave to arrive at a focal point from each element, based on a distance between the focal point and the element, a phase is calculated for each element to compensate for the time difference between sound waves generated by the respective elements.

A user is enabled to determine amplitude of the particle velocity to create a desired sound pressure $P_{HOMO}$ at a focal point position. For example, when an amplitude is input through the interface unit 110, the parameter determiner 130 calculates the sound pressure $P_{HOMO}$ exerted by the N elements at the m-th focal point position using a Rayleigh-Sommerfeld integral as defined by Equation (4). Furthermore, the user may adjust the amplitude so as to create the desired sound pressure $P_{HOMO}$.

Although the parameter determiner 130 calculates the sound pressure PHOMO using the Rayleigh-Sommerfeld integral, the embodiment is not limited thereto.

$$\sum_{n=1}^{N} u_n \frac{jk}{2\pi} \int_{S_n} \frac{\rho c e^{-j\alpha k |r_m - r_n|}}{|r_m - r_n|} dS_n = p_{HOMO}(r_m) \quad (4)$$

where k is a wave number of therapeutic ultrasound and is related to a wavelength of ultrasound using the equation $k=2\pi/\lambda$, and $\alpha$, $\rho$, and c are attenuation coefficients of a homogeneous tissue, a density of the tissue, and a speed of a sound wave, respectively.

Sn, un, and $P_{HOMO}(r_m)$ are cross-sectional areas of an n-th element, a particle velocity for the n-th element, and a sound pressure at a focal point position having a position vector of $r_m$, respectively. The particle velocity $u_n$ is precalculated so as to create a focal point at a desired position in the homogeneous tissue.

At operation 1020, the method at the parameter determiner 130 sets elements that will transmit therapeutic ultrasound among the elements in the therapeutic ultrasound irradiation device 30 and arbitrarily sets a particle velocity of each of the set elements. For instance, the parameter determiner 130 uses a generic operator to set some or all of the N elements in the therapeutic ultrasound irradiation device 30 as elements to transmit the therapeutic ultrasound. The parameter determiner 130 sets particle velocities of the respective set elements and combines the particle velocities with one another. A particle velocity u that will be described below is the combined particle velocity obtained by the parameter determiner 130.

At operation 1030, the method at the parameter determiner 130 calculates a sound pressure $P_{HET}$ at a focal point position under the assumption that therapeutic ultrasound having the combined particle velocity u obtained at operation 1020 propagates through heterogeneous tissue. The heterogeneous tissue refers to a tissue that reflects characteristics of one or more tissues on a path along which therapeutic ultrasound propagates. The characteristics calculation unit 120 calculates characteristics, which may include a density of each tissue and the speed and attenuation coefficient of therapeutic ultrasound waves within the tissue.

For example, the parameter determiner 130 calculates a sound pressure $P_{HET}(r_m)$ at a focal point position having a position vector of $r_m$, which reflects characteristics of the heterogeneous tissue, using an angular spectrum method (ASM). The ASM involves expanding a complex wave field into a sum of an infinite number of plane waves. When a medium on the propagation path of therapeutic ultrasound is heterogeneous, the parameter determiner 130 calculates a sound pressure $P_{HET}(r_m)$ using the ASM as follows:

Referring back to FIG. 5, when a plurality of different media, for instance, internal tissues, are located on the propagation path of therapeutic ultrasound, the parameter determiner 130 calculates a transmitted acoustic field $w_{1b}$ that passes through a discontinuous boundary $D_1$ of a medium by combining an incident acoustic field, $w_{1f}$, incident on the boundary $D_1$ with a transmission coefficient T. The parameter determiner 130 then applies a 2D Fourier Transform to the transmitted acoustic field $w_{1b}$ to compute an angular spectrum $W_{1b}$ in a plane $D_1$. Then, the parameter determiner 130 calculates an angular spectrum $W_2$ by correcting a phase change due to a distance difference between planes $D_1$ and $D_2$ based on the angular spectrum $W_{1b}$. Thereafter, the parameter determiner 130 applies a 2D Inverse Fourier Transform to the angular spectrum $W_2$ to calculate an acoustic field $w_2$ in a plane $D_2$.

The parameter determiner 130 repeats the above operations a predetermined number of times corresponding to the number of boundaries on the propagation path of the therapeutic ultrasound to calculate the sound pressure $P_{HET}(r_m)$ at a position of the focal point 560 having a position vector of $r_m$, which reflects characteristics of the heterogeneous tissue. Although the parameter determiner 130 calculates the sound pressure $P_{HET}(r_m)$ by using the ASM, the embodiment is not limited thereto.

At operation 1040, the method at the parameter determiner 130 determines whether a difference between the sound pressures $P_{HOMO}$ and $P_{HET}$ calculated in operations 1010 and 1030, respectively, is less than a predetermined threshold value. The predetermined threshold value may be automatically determined by the method at the parameter determiner 130 or determined by a user through the interface unit 110. In response to the difference between the sound pressures $P_{HOMO}$ and $P_{HET}$ being less than or equal to the predetermined threshold value, the method at the parameter determiner 130 determines the particle velocity, u, of the elements as a final value. However, when the difference exceeds the threshold, the method proceeds to operation 1050.

At operation 1050, the method at the parameter determiner 130 resets a particle velocity of each of the elements that are selected among the elements in the therapeutic ultrasound irradiation device 30 to transmit therapeutic ultrasound. The method at the parameter determiner 130 then combines particle velocities of the set elements with one another and returns to operations 1030 and 1040.

After determining a parameter, for instance, a particle velocity of an element to transmit therapeutic ultrasound to a focal point by performing operations 1010 through 1050 as described above, the method at the parameter determiner 130 transmits the determined parameter to the control unit 140.

While FIG. 10 shows that the parameter of therapeutic ultrasound is set so that a difference between the sound pressure $P_{HOMO}$ in a homogeneous medium and the sound pressure $P_{HET}$ in a heterogeneous medium is less than or equal to a predetermined threshold, other methods may be used. Another method of setting a parameter of therapeutic ultrasound in the parameter determiner 130 will now be described in detail with reference to FIG. 11.

Figure 11:
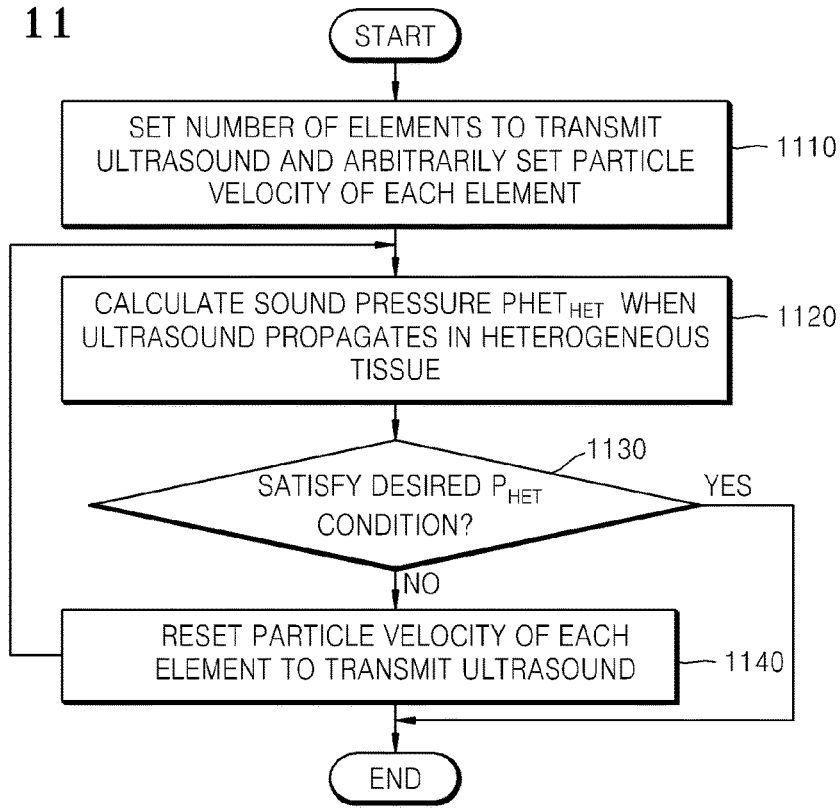
FIG. 11 is a flowchart of another operation of a parameter determiner, according to an embodiment.

FIG. 11 is a flowchart of another example of operation of the parameter determiner 130, in accord with an embodiment.

The method at the parameter determiner 130 may determine a parameter of therapeutic ultrasound using a sound pressure $P_{HET}$ in a heterogeneous medium without comparing the sound pressure $P_{HET}$ with a sound pressure $P_{HOMO}$ in a homogeneous medium. In other words, by repeating setting of the parameter of therapeutic ultrasound until the desired sound pressure $P_{HET}$ is created in a heterogeneous medium, an operation of comparing the sound pressure $P_{HET}$ with a sound pressure $P_{HOMO}$ in a homogeneous medium may be omitted.

Referring to FIG. 11, at operation 1110, the method at the parameter determiner 130 sets elements to transmit therapeutic ultrasound among the elements in the therapeutic ultrasound irradiation device 30 and arbitrarily sets a particle velocity of each of the set elements. The process at the parameter determiner 130 combines particle velocities of the respective set elements with one another. The method at the parameter determiner 130 sets particle velocities of the respective set elements and combines the particle velocities with one another.

At operation 1120, the method at the parameter determiner 130 calculates a sound pressure $P_{HET}$ at a position of a focal point that the therapeutic ultrasound, which includes the combined particle velocity u obtained at operation 1110, propagates through a heterogeneous tissue.

At operation 1130, the parameter determiner 130 determines whether the sound pressure $P_{HET}$ satisfies a predetermined condition. When the sound pressure $P_{HET}$ satisfies the predetermined condition, the parameter determiner 130 determines the particle velocity of the elements as a final value. On the other hand, when the sound pressure $P_{HET}$ does not satisfy the predetermined condition, the method proceeds to operation 1140.

At operation 1140, the method at the parameter determiner 130 resets a particle velocity of each of the elements that are selected among the elements in the therapeutic ultrasound irradiation device 30 to transmit the therapeutic ultrasound. The parameter determiner 130 then combines particle velocities of the set elements with one another and returns to the operations 1120 and 1130.

Referring back to FIG. 2, the control unit 140 generates a control signal for an element of the therapeutic ultrasound irradiation device 30. In one example, the control signal is the particle velocity u of the elements that transmit therapeutic ultrasound. The control unit 140 then transmits the control signal to the therapeutic ultrasound irradiation device 30.

As described above, the parameter determiner 130 determines a parameter by combining the characteristics of therapeutic ultrasound, transmitted through elements of the therapeutic ultrasound irradiation device 30, and characteristics calculated in the calculator 124, which may affect the propagation of the therapeutic ultrasound. As a result, the parameter determiner 130 enables automatic transformation of the characteristics of tissues into characteristics of the therapeutic ultrasound.

Figure 8:
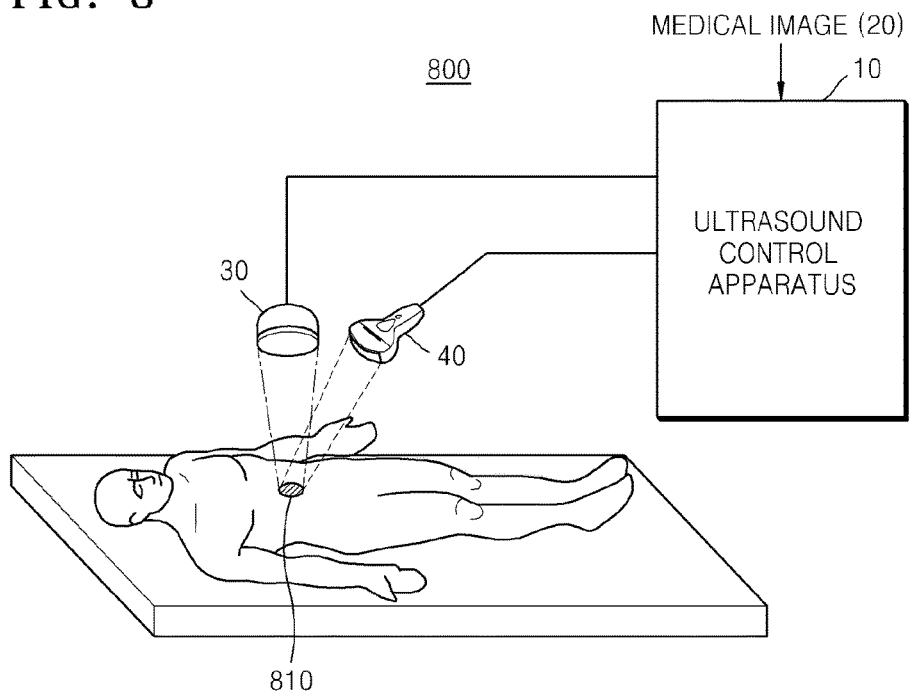
FIG. 8 illustrates a construction of a high intensity focused ultrasound (HIFU) system, according to an embodiment.

FIG. 8 illustrates a configuration of a HIFU system 800, according to an embodiment. Referring to FIG. 8, the HIFU system 800 includes an ultrasound control apparatus 10, a therapeutic ultrasound irradiation device 30, and a diagnostic ultrasound irradiation device 40.

Although the HIFU system 800 of FIG. 8 includes certain components related to the embodiment, it will be understood by those skilled in the art that the HIFU system 800 may further include less or more components than the components shown in FIG. 8.

Furthermore, the HIFU system 800 includes the ultrasound control apparatus 10 shown in FIGS. 1, 2, and 4. Thus, the descriptions of the ultrasound control apparatus 10 with reference to FIGS. 1, 2, and 4 may apply to the HIFU system 800 of FIG. 8, and, thus, are not repeated.

The HIFU system 800 focuses therapeutic ultrasound on a focal point using the therapeutic ultrasound irradiation device 30. For example, the HIFU system 800 controls the therapeutic ultrasound irradiation device 30 to transmit therapeutic ultrasound using an externally input medical image 20 and an ultrasound image generated by the diagnostic ultrasound irradiation device 40 transmitting diagnostic ultrasound to a subject 810.

The HIFU system 800 is configured to generate therapeutic ultrasound by reflecting heterogeneity in characteristics of one or more tissues on a path along which the therapeutic ultrasound propagates, so that a focal point is formed accurately at a desired position. The HIFU system 800 may also generate therapeutic ultrasound by reflecting an examinee's characteristics, thereby minimizing a variation in treatment effects among examinees or patients.

The diagnostic ultrasound irradiation device 40 transmits diagnostic ultrasound to the subject 810 and acquires a reflected ultrasound signal to generate an ultrasound image of the subject 810. The diagnostic ultrasound irradiation device 40 processes the acquired reflected ultrasound signal to generate an ultrasound image of the subject 810.

The ultrasound control apparatus 10 calibrates the therapeutic ultrasound irradiation device 30 using an image obtained by registering the medical image 20 containing anatomical information about the subject 810 with the ultrasound image, and generates a control signal to generate therapeutic ultrasound that the calibrated therapeutic ultrasound irradiation device will transmit to a focal point.

The ultrasound control apparatus 10 generates therapeutic ultrasound by automatically reflecting characteristics of the one or more tissues in a path along which the therapeutic ultrasound will propagate, thereby allowing the therapeutic ultrasound irradiation device 30 to focus the therapeutic ultrasound at a desired position without user intervention.

Furthermore, the ultrasound control apparatus 10 enables treatment of one or more tissues with a single surgical procedure.

The therapeutic ultrasound irradiation device 30 uses the control signal generated by the ultrasound control apparatus 10 to transmit the therapeutic ultrasound towards a position of a focal point.

Figure 9:
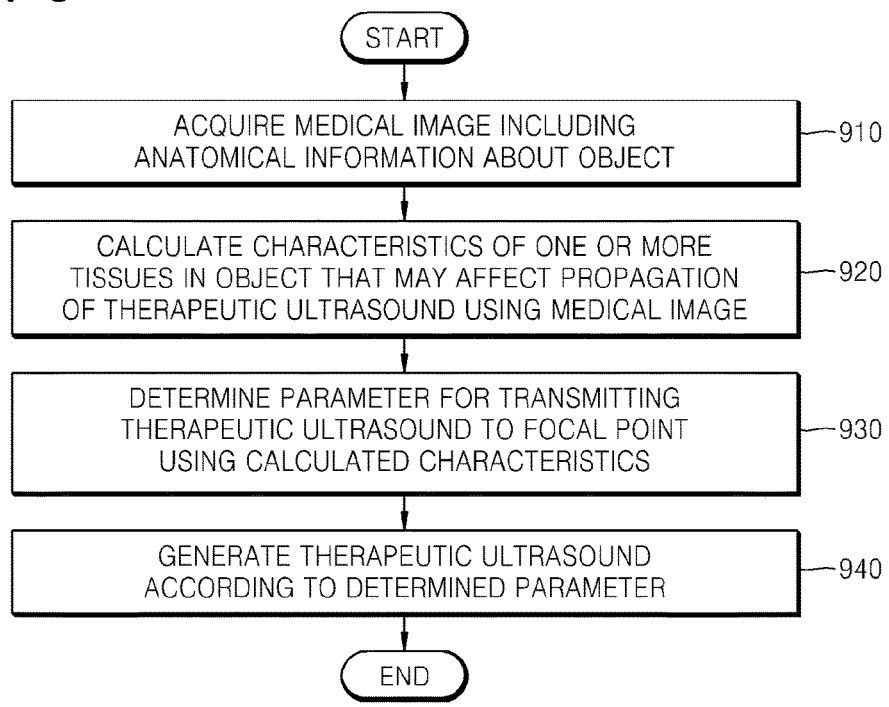
FIG. 9 is a flowchart of a method to generate therapeutic ultrasound, according to an embodiment.

FIG. 9 is a flowchart of a method to generate therapeutic ultrasound to be transmitted from a therapeutic ultrasound irradiation device, according to an embodiment. Referring to FIG. 9, the method to generate therapeutic ultrasound includes operations that are performed in a time series by the ultrasound control apparatus 10 shown in FIGS. 1, 2, and 4 or by the HIFU system 800 in FIG. 8. Thus, although omitted hereinafter, the above descriptions of the ultrasound control apparatus 10 or the HIFU system 800 with reference to FIGS. 1, 2, 4, and 8 may apply to the method to generate therapeutic ultrasound illustrated in FIG. 9.

At operation 910, the method at the interface unit 110 acquires a medical image including anatomical information of a subject.

At operation 920, the method at the characteristics calculation unit 120 calculates characteristics of one or more tissues in a subject, which may affect the propagation of therapeutic ultrasound, using the medical image acquired at operation 910. More specifically, the method at the characteristics calculation unit 120 uses the acquired medical image to calculate characteristics of the one or more tissues on a path along which therapeutic ultrasound propagates from an element of the therapeutic ultrasound irradiation device 30 to a focal point.

For example, the method at the characteristics calculation unit 120 may generate models for characteristics of each of the tissues that construct the subject and calculate the characteristics of the one or more tissues on the propagation path by using the generated models.

The method at the characteristics calculation unit 120 also acquires the medical image and an ultrasound image of the subject from the interface unit 110 and registers the medical image with the ultrasound image. The method at the characteristics calculation unit 120 then calibrates the diagnostic ultrasound irradiation device 40 using an image obtained after the registration, and generates a signal to calibrate the therapeutic ultrasound irradiation device using the calibrated diagnostic ultrasound irradiation device 40.

At operation 930, the method at the parameter determiner 130 determines a parameter of therapeutic ultrasound to create a focal point on a subject using the characteristics calculated in operation 920.

At operation 940, the method at the control unit 140 produces a control signal to generate the therapeutic ultrasound according to the parameter determined at operation 930.

The ultrasound control apparatus 10 and the HIFU system 800, according to various embodiments, enable irradiation of therapeutic ultrasound by reflecting heterogeneity in characteristics of one or more tissues in a path along which the therapeutic ultrasound propagates, thereby improving the accuracy of treatment using HIFU.

The ultrasound control apparatus 10 and the HIFU system 800 are also configured to automatically reflect characteristics of tissues encountered on a travel path of the therapeutic ultrasound at a parameter to transmit the therapeutic ultrasound. Thus, the ultrasound control apparatus 10 and HIFU system 800 generate therapeutic ultrasound to create a focal point accurately at a desired position without user intervention.

The ultrasound control apparatus 10 and the HIFU system 800 may also individually generate therapeutic ultrasound by reflecting individual examinee tissue characteristics, thereby minimizing a variation in HIFU treatment effects among examinees or patients.

In addition, the ultrasound control apparatus 10 and the HIFU system 800 may generate therapeutic ultrasound by reflecting characteristics of tissues along a travel path of the therapeutic ultrasound, thereby allowing treatment of one or more organs with a single surgical procedure.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. These terms do not necessarily imply a specific order or arrangement of the elements, components, regions, layers and/or sections. Thus, a first element, component, region, layer or section discussed below could be termed a second element, component, region, layer or section without departing from the teachings description of the present invention.

The units described herein may be implemented using hardware components, including, but not limited to a processing device. Examples of such units include, but are not limited to, interface unit 110, characteristics calculation unit 120, parameter determiner 130, control unit 140, calibration unit 150.The processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

Program instructions to perform methods described in FIGS. 3 and 9-11, or one or more operations thereof, may be recorded, stored, or fixed in one or more non-transitory computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method to generate a therapeutic ultrasound wave from a therapeutic ultrasound irradiation device, the method comprising:
   acquiring a medical image comprising anatomical information about a subject using a processor;
   calculating one or more characteristics of a heterogeneous tissue in the subject affecting propagation of the therapeutic ultrasound wave based on the medical image using the processor;
   determining a parameter of the therapeutic ultrasound wave, using the processor, to create a focal point on the subject using the one or more calculated characteristics; and
   generating the therapeutic ultrasound wave at the therapeutic ultrasound irradiation device, using a signal from the processor, the signal determined according to the determined parameter,
   wherein the determining of the parameter comprises:
      setting a particle velocity of the therapeutic ultrasound wave;
      calculating, using the processor, a sound pressure at the focal point that the therapeutic ultrasound wave propagates through the heterogeneous tissue, based on the one or more calculated characteristics of the heterogeneous tissue;
      determining, using the processor, whether the sound pressure satisfies a predetermined pressure condition; and
      resetting, using the processor, the particle velocity of the therapeutic ultrasound wave, in response to the sound pressure not satisfying the predetermined pressure condition.

2. The method of claim 1, wherein the calculating of the one or more characteristics using the processor comprises:
   processing, using the processor, the medical image to calculate the one or more characteristics of the tissue on a path along which the therapeutic ultrasound wave propagates from an element of the therapeutic ultrasound irradiation device to the focal point.

3. The method of claim 1, wherein the one or more characteristics comprise a speed of the therapeutic ultrasound wave passing through the tissue, a density of the tissue, an attenuation coefficient of the therapeutic ultrasound wave for the tissue, and a combination thereof.

4. The method of claim 1, further comprising:
   calibrating, using the processor, the focal point using the medical image.

5. The method of claim 1, wherein the calculating of the one or more characteristics using the processor, further comprises:
   processing, using the processor, the medical image to calculate the one or more characteristics of the tissue along a path that the therapeutic ultrasound wave propagates from an element of the therapeutic ultrasound irradiation device to the focal point.

6. The method of claim 4, wherein the calibrating of the therapeutic ultrasound irradiation device using the processor, comprises:
   generating an ultrasound image of the subject using a diagnostic ultrasound irradiation device;
   calibrating the diagnostic ultrasound irradiation device using an image obtained by registering the ultrasound image with the medical image; and
   calibrating the therapeutic ultrasound irradiation device using the calibrated diagnostic ultrasound irradiation device.

7. The method of claim 4, wherein the calibration of the therapeutic ultrasound irradiation device using the processor is performed by adjusting coordinates of the therapeutic ultrasound irradiation device.

8. The method of claim 1, wherein the medical image comprises a computed tomography (CT) image.

9. The method of claim 1, wherein the determining of the parameter of the therapeutic ultrasound wave using the processor comprises:
   combining characteristics of the therapeutic ultrasound wave with the calculated characteristics of the tissue affecting the propagation of the therapeutic ultrasound wave.

10. An apparatus to generate a therapeutic ultrasound wave, the apparatus comprising:
    one or more processors configured to:
       acquire a medical image comprising anatomical information about a subject;
       calculate one or more characteristics of a heterogeneous tissue in the subject affecting propagation of the therapeutic ultrasound wave based on the medical image;
       determine a parameter of the therapeutic ultrasound wave to create a focal point on the subject using the one or more calculated characteristics; and
       produce a control signal according to the determined parameter, and
    a therapeutic ultrasound irradiation device configured to generate the therapeutic ultrasound wave directed at the focal point,
    wherein the one or more processors are configured to determine the parameter of the therapeutic ultrasound wave by:
       setting a particle velocity of the therapeutic ultrasound wave;
       calculating a sound pressure at the focal point that the therapeutic ultrasound wave propagates through the heterogeneous tissue, based on the one or more calculated characteristics of the heterogeneous tissue;
       determining whether the sound pressure satisfies a predetermined pressure condition; and
       resetting the particle velocity of the therapeutic ultrasound wave, in response to the sound pressure not satisfying the predetermined pressure condition.

11. The apparatus of claim 10, wherein the one or more processors are configured to calculate the characteristics of the tissues by processing the medical image on a path along which the therapeutic ultrasound wave propagates from an element of the therapeutic ultrasound irradiation device to the focal point.

12. The apparatus of claim 10, wherein the one or more characteristics comprise a speed of the therapeutic ultrasound wave passing through the tissue, a density of the tissue, an attenuation coefficient of the therapeutic ultrasound wave for the tissue, and a combination thereof.

13. The apparatus of claim 10, wherein the one or more processors are further configured to calibrate the apparatus using the medical image, the calibrating of the apparatus comprising adjusting coordinates of the focal point.

14. The apparatus of claim 13, wherein the one or more processors acquire an ultrasound image of the subject, calibrate a diagnostic ultrasound irradiation device by using an image obtained by registering the ultrasound image with the medical image, and calibrate the focal point of the therapeutic ultrasound irradiation device using the calibrated diagnostic ultrasound irradiation device.

15. The apparatus of claim 10, wherein the medical image includes a computed tomography (CT) image.

16. A non-transitory computer-readable recording medium having recorded thereon a program, which, when executed by one or more processors, cause the one or more processors to implement the method of claim 1.

17. A method to generate an therapeutic ultrasound wave, the method comprising:
   acquiring an image of a subject, using a processor, the image of the subject including heterogeneous tissue;
   calculating characteristics of the heterogeneous tissue affecting propagation of the therapeutic ultrasound wave using the image;
   determining a parameter of the therapeutic ultrasound wave, using a processor, in which the calculated characteristics of the heterogeneous tissue have been incorporated using the image; and
   generating the therapeutic ultrasound wave from a therapeutic ultrasound irradiation device using a signal from the processor determined according to the determined parameter,
   wherein the determining of the parameter comprises:
      calculating, using the processor, a first sound pressure representing a sound pressure at a focal point upon the therapeutic ultrasound wave propagating in a homogeneous tissue;
      setting a particle velocity of an element transmitting the ultrasound among elements in the ultrasound irradiation device;
      calculating, using the processor, a second sound pressure representing a sound pressure at the focal point upon the therapeutic ultrasound wave using the particle velocity propagating in the heterogeneous tissue;
      determining, using the processor, whether a difference between the first and second sound pressures exceeds a threshold value; and
      resetting, using the processor, a particle velocity of an element transmitting the therapeutic ultrasound wave in response to the difference exceeding the threshold value.

18. The method of claim 17, wherein the image of the subject includes human internal organs.

19. The method of claim 17, wherein the determining of the parameter of the therapeutic ultrasound wave, using the processor, further comprises
   determining the parameter of the therapeutic ultrasound wave to create the focal point on the subject using the calculated characteristics.

20. The method of claim 19, wherein the determining of the parameter of the therapeutic ultrasound wave using the calculated characteristics, using the processor, comprises
   determining the parameter of the therapeutic ultrasound wave based on a difference between the first sound pressure and the second sound pressure.

21. A therapeutic ultrasound control apparatus, comprising:
   one or more processors configured to process a medical image of a subject to determine a parameter of a therapeutic ultrasound wave based on a speed of a therapeutic ultrasound wave passing through a heterogeneous tissue, a density of the heterogeneous tissue, and an attenuation coefficient of the therapeutic ultrasound wave passing through the heterogeneous tissue, and to control the therapeutic ultrasound wave to create a focal point onto a subject; and
   a controller producing a signal used to generate the therapeutic ultrasound wave according to the determined parameter,
   wherein the one or more processors are configured to:
      calculate a first sound pressure representing a sound pressure at a focal point upon the therapeutic ultrasound wave propagating in a homogeneous tissue,
      set a particle velocity of an element transmitting the ultrasound among elements in the ultrasound irradiation device;
      calculate a second sound pressure representing a sound pressure at the focal point upon the therapeutic ultrasound wave using the particle velocity propagating in the heterogeneous tissue,
      determine whether a difference between the first and second sound pressures exceeds a threshold value, and
      reset a particle velocity of an element transmitting the therapeutic ultrasound wave in response to the difference exceeding the threshold value.

22. The apparatus of claim 21, wherein the one or more processors are further configured to control an intensity and a duration of the therapeutic ultrasound wave.

23. The apparatus of claim 21, wherein the one or more processors are further configured to process the medical image to calibrate coordinates of the focal point of the therapeutic ultrasound wave.

* * * * *